(12) United States Patent
Sarama et al.

(10) Patent No.: US 6,794,375 B2
(45) Date of Patent: Sep. 21, 2004

(54) PALATABLE ARGININE COMPOUNDS AND USES THEREOF FOR CARDIOVASCULAR HEALTH

(75) Inventors: Robert Joseph Sarama, Loveland, OH (US); Raymond Louis Niehoff, West Chester, OH (US)

(73) Assignee: The Procter & Gamble Co., Cincinnati, OH (US)

( * ) Notice: Subject to any disclaimer, the term of this patent is extended or adjusted under 35 U.S.C. 154(b) by 0 days.

(21) Appl. No.: 10/181,655

(22) PCT Filed: Jan. 25, 2001

(86) PCT No.: PCT/US01/02384

§ 371 (c)(1),
(2), (4) Date: Jul. 19, 2002

(87) PCT Pub. No.: WO01/55098

PCT Pub. Date: Aug. 2, 2001

(65) Prior Publication Data

US 2003/0113361 A1 Jun. 19, 2003

Related U.S. Application Data

(60) Provisional application No. 60/178,723, filed on Jan. 28, 2000.

(51) Int. Cl.[7] .......................... A61K 31/56; A23L 1/302
(52) U.S. Cl. ............................ 514/182; 426/72; 426/73
(58) Field of Search ........................ 552/544; 514/182; 426/72, 73

(56) References Cited

U.S. PATENT DOCUMENTS

| | | |
|---|---|---|
| 2,661,349 A | 12/1953 | Caldwell et al. |
| 3,004,043 A | 10/1961 | Stern |
| 3,085,939 A | 4/1963 | Wruble et al. |
| 3,455,838 A | 7/1969 | Marotta et al. |
| 3,579,548 A | 5/1971 | Whyte |
| 3,751,569 A | 8/1973 | Erickson |
| 3,865,939 A | 2/1975 | Jandacek |
| 4,195,084 A | 3/1980 | Ong |
| 4,338,346 A | 7/1982 | Brand |
| 4,399,163 A | 8/1983 | Brennan et al. |

(List continued on next page.)

FOREIGN PATENT DOCUMENTS

| | | |
|---|---|---|
| DE | 197 50 422 C1 | 11/1998 |
| DE | 198 00 812 A1 | 7/1999 |
| EP | 0 168 112 | 1/1986 |
| EP | 0 289 636 | 11/1988 |
| EP | 0 320 976 A1 | 6/1989 |
| EP | 0 546 796 | 6/1993 |
| EP | 0 567 433 A1 | 10/1993 |
| JP | 58134197 | 8/1983 |
| JP | 58203982 | 11/1983 |
| JP | 9241156 | * 9/1997 |
| JP | 11193264 | 7/1999 |
| JP | 2000128725 | 5/2000 |
| WO | WO 94/06450 | 3/1994 |
| WO | WO 94/18225 | 8/1994 |
| WO | WO 95/01172 | 1/1995 |
| WO | WO 95/08342 | 3/1995 |
| WO | WO 96/34858 | 11/1996 |
| WO | WO 97/42830 | 11/1997 |
| WO | WO 98/01126 | 1/1998 |
| WO | WO 98/06405 | 2/1998 |
| WO | WO 98/28990 | 7/1998 |
| WO | WO 99/30576 | 6/1999 |

OTHER PUBLICATIONS

US 4,461,762, 7/1984, Malinow (withdrawn)
XP–000999672—"Diet and Coronary Heart Disease: Beyond Dietary Fats and Low–Denistiy–Lipoprotein Cholesterol"; Am. J. Clin. Nutr., 1994; 599suppl):1117S–23S.

(List continued on next page.)

Primary Examiner—Barbara P. Badio
(74) Attorney, Agent, or Firm—Bryn T. Lorentz; S. Robert Chuey

(57) ABSTRACT

The present invention is directed to a compound having the structure (I): and acceptable salts, polypeptides, and pro-forms thereof, wherein R is selected from the group consisting of: (a) substituted glycerols; wherein n is an integer from 1 to 2; (b) vitamins; wherein n is 1; (c) sterols; wherein n is 1; (d) stanols; wherein n is 1; and (e) $C_6$–$C_{32}$ alkyl; and (f) $C_6$–$C_{32}$ alkenyl; wherein n is 1. The present invention is further directed to compositions and kits comprising these compounds as well as methods of using the compounds. The compounds, compositions, kits, and methods herein are useful for providing general health benefits to the consumer, particularly cardiovascular benefits, anti-menopausal benefits and/or treating sexual dysfunction (particularly, erectile dysfunction). Most particularly, the compounds, compositions, kits, and methods herein are useful for providing cardiovascular benefits, including lowering cholesterol in the consumer, treating, preventing, and/or inhibiting heart disease (e.g., atherosclerosis, restenosis, thrombosis) and, for example, treating other conditions such as hypercholesterolemia, hypertension, poor circulation,

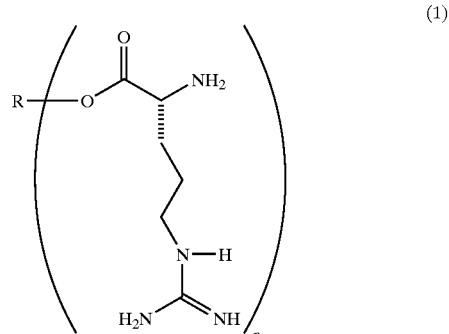

(1)

and complications associated with diabetes.

7 Claims, No Drawings

U.S. PATENT DOCUMENTS

| | | | |
|---|---|---|---|
| 4,411,925 A | 10/1983 | Brennan et al. |
| 4,420,432 A | 12/1983 | Chibata et al. |
| 4,423,029 A | 12/1983 | Rizzi |
| 4,455,333 A | 6/1984 | Hong et al. |
| 4,460,617 A | 7/1984 | Barndt et al. |
| 4,524,067 A | 6/1985 | Arichi et al. |
| 4,582,715 A | 4/1986 | Volpenhein |
| 4,582,927 A | 4/1986 | Fulcher |
| 4,599,152 A | 7/1986 | Ashmead |
| 4,602,003 A | 7/1986 | Malinow |
| 4,680,290 A | 7/1987 | Cassal |
| 4,705,690 A | 11/1987 | Brand et al. |
| 4,705,691 A | 11/1987 | Kupper et al. |
| 4,737,375 A | 4/1988 | Nakel et al. |
| 4,786,510 A | 11/1988 | Nakel et al. |
| 4,786,518 A | 11/1988 | Nakel et al. |
| 4,830,716 A | 5/1989 | Ashmead |
| 4,863,898 A | 9/1989 | Ashmead et al. |
| 4,920,098 A | 4/1990 | Cotter et al. |
| 4,946,701 A | 8/1990 | Tsai et al. |
| 4,994,283 A | 2/1991 | Mehansho et al. |
| 5,032,608 A | 7/1991 | Dudrick |
| 5,108,761 A | 4/1992 | Andon et al. |
| 5,112,815 A | 5/1992 | Ambrus et al. |
| 5,118,513 A | 6/1992 | Mehansho et al. |
| 5,128,374 A | 7/1992 | Kochanowski |
| 5,151,274 A | 9/1992 | Saltman et al. |
| 5,157,022 A | 10/1992 | Barbul |
| 5,186,965 A | 2/1993 | Fox et al. |
| 5,215,769 A | 6/1993 | Fox et al. |
| 5,217,997 A | 6/1993 | Levere et al. |
| 5,225,221 A | 7/1993 | Camden et al. |
| 5,232,709 A | 8/1993 | Saltman et al. |
| 5,244,887 A | 9/1993 | Straub |
| 5,270,041 A | 12/1993 | Eugster et al. |
| 5,306,514 A | 4/1994 | Letton et al. |
| 5,306,515 A | 4/1994 | Letton et al. |
| 5,314,919 A | 5/1994 | Jacobs |
| 5,364,884 A | 11/1994 | Varma et al. |
| 5,385,940 A | 1/1995 | Moskowitz |
| 5,389,387 A | 2/1995 | Zuniga et al. |
| 5,401,524 A | 3/1995 | Burkes et al. |
| 5,419,925 A | 5/1995 | Seiden et al. |
| 5,422,128 A | 6/1995 | Burkes et al. |
| 5,422,131 A | 6/1995 | Elsen et al. |
| 5,424,082 A | 6/1995 | Dake et al. |
| 5,427,806 A | 6/1995 | Ekanayake et al. |
| 5,428,070 A | 6/1995 | Cooke et al. |
| 5,433,965 A | 7/1995 | Fischer et al. |
| 5,445,837 A | 8/1995 | Burkes et al. |
| 5,451,416 A | 9/1995 | Johnston et al. |
| 5,468,506 A | 11/1995 | Andon |
| 5,474,793 A | 12/1995 | Meyer et al. |
| 5,571,441 A | 11/1996 | Andon et al. |
| 5,591,836 A | 1/1997 | Mazur et al. |
| 5,612,026 A | 3/1997 | Diehl |
| 5,670,344 A | 9/1997 | Mehansho et al. |
| 5,780,039 A | 7/1998 | Greenberg et al. |
| 5,843,499 A | 12/1998 | Moreau et al. |
| 5,958,913 A | 9/1999 | Miettenen et al. |
| 6,063,428 A | 5/2000 | Ekanayake et al. |

OTHER PUBLICATIONS

XP–001000550—"Chemical Composition of Cassia Holosericae"; J. Pharm. Univ. Karachi; vol. 3, No. 2, pp. 101–104, 1985.

XP–002165058—"Preparation of amino acids and peptide derivatives as chemokine receptor antagonists"; Chemical Abstracts, Columbus, Ohio, 131:102544, 1999.

XP–002165059—"Enzymic synthesis of arginine–based cationic surfactants"; Chemical Abstracts, Columbus, Ohio, 130:339707, 1999.

XP–002165061—"Cationic surfactant compositions"; Chemical Abstracts, Columbus, Ohio, 100:70352, 1984.

XP002165062—"Inhibition of serine proteases by low molecular weight peptides and their derivatives"; Chemical Abstracts, Columbus, Ohio, 95:164539, 1981.

XP–002165063—"Skin conditioners containing arginine derivatives"; Chemical Abstracts, Columbus, Ohio, 132:325831, 2000.

XP–002165064—"Long chain arginine esters"; Chemical Abstracts, Columbus, Ohio, 132:339176, 2000.

XP–002165065—WPI Abstract, AN–1997–021670.

XP–002165066—WPI Abstract, AN–1997–508789.

XP–002165167—"Vitamin E amino acid esters"; Chemical Abstracts, Columbus, Ohio, 100:210216.

Kochhar, S.P.—"Influence of Processing on Sterols of Edible Vegetable Oils", Prog. Lipid Res., vol. 22, pp. 161–188.

\* cited by examiner

PALATABLE ARGININE COMPOUNDS AND USES THEREOF FOR CARDIOVASCULAR HEALTH

REFERENCE TO PRIORITY APPLICATION

The present invention is a 371 of PCT/US01/02384 filed Jan. 25, 2001 and claims priority to U.S. Provisional Application Serial No. 60/178,723, filed Jan. 28, 2000.

FIELD OF THE INVENTION

The present invention relates to compounds, compositions, kits, and methods which are useful for providing various general health benefits including, but not limited to cardiac benefits, including lowering cholesterol in the consumer, treating, preventing, and/or inhibiting heart disease (e.g., atherosclerosis, restenosis, thrombosis) and, treating conditions such as hypercholesterolemia, hypertension, poor circulation, and complications associated with diabetes.

BACKGROUND OF THE INVENTION

Cardiovascular conditions, including heart disease, hypercholesterolemia, hypertension, poor circulation, and complications associated with diabetes, are serious medical conditions which are leading causes of mortality in humans. Various regimens have been suggested for prevention and treatment of these conditions, including pharmaceutical, dietary, and exercise regimens. Notwithstanding, they remain among the most prevalent and serious of all medical conditions.

L-arginine is a natural amino acid which has been identified to provide certain general health benefits including, for example, cardiovascular benefits, such as lowering cholesterol in the consumer, and treating, preventing, and/or inhibiting heart disease and poor circulation. See e.g., Moskowitz, U.S. Pat. No. 5,385,940, assigned to The General Hospital Corp., issued Jan. 31, 1995; Sonaka et al., EP 0,546,796, assigned to Ajinomoto Co., published Jun. 16, 1993; Cotter et al., U.S. Pat. No. 4,920,098, assigned to Baxter International Inc., issued Apr. 24, 1990; Dudrick, U.S. Pat. No. 5,032,608, issued Jul. 16, 1991; Levere et al., U.S. Pat. No. 5,217,997, issued Jun. 8, 1993; Cooke et al., U.S. Pat. No. 5,428,070, assigned to Stanford University, issued Jun. 27,1995; Chibata et al., U.S. Pat. No. 4,420,432, assigned to Tanabe Seiyaky Co., issued Dec. 13, 1983; Varma et al., U.S. Pat. No. 5,364,884, assigned to Baylor College of Medicine, issued Nov. 15, 1994; and Barbul, U.S. Pat. No. 5,157,022, issued Oct. 20, 1992.

The utility of L-arginine, particularly to advance cardiovascular health, is therefore well known in the art. However, as for any beneficial regimen, compliance must be assured in order to realize the various benefits thereof. Unfortunately, L-arginine and its close derivatives (including salts, polypeptides, and pro-forms) have a strong, bitter, and fishy flavor, making L-arginine generally unacceptable for use. This results in decreased compliance of a regimen involving L-arginine, and the requisite cardiovascular benefits are therefore not realized. Accordingly, to enhance compliance, it would be desirable to provide L-arginine in a form which diminishes and/or removes the unacceptable flavor associated with L-arginine.

Unfortunately, flavor improvement is typically associated with a decrease in the general health benefits of the component which is desired to be delivered. Additionally, because delivery of relatively large amounts of L-arginine is desirable (erg., about 3 grams to about 10 grams of L-arginine per dose), it becomes increasingly more difficult to mask the strong, bitter, and fishy flavor. Such difficulties manifest themselves in the marketplace, where it is understood that current products containing L-arginine are not acceptable to the consumer due to unacceptable flavor.

The present inventors have surprisingly discovered that the unacceptable flavor of L-arginine is significantly improved through esterification of the L-arginine with any of various components, which will be defined herein. Interestingly, and quite unexpectedly, the esterified L-arginine exhibits significantly improved flavor relative to L-arginine itself. The improvement has been found particularly significant, wherein the component is lipophilic in nature. Accordingly, such combination is acceptable to consumers which, more importantly, translates into improved regimen compliance and enhanced cardiovascular, and other health, benefits. Additionally, the in vivo hydrolysis products of the ester are biologically acceptable and, in many cases, provide unique health benefits which supplement those of L-arginine.

The foregoing findings are unexpected relative to the known literature. Accordingly, the present inventors have discovered compounds, compositions, and kits which provide general health benefits, including cardiovascular benefits. Relative to known products, compliance is improved and/or ensured through use of such compositions because the flavor is acceptable to the consumer. The compositions are easily provided as a pharmaceutical, food, or beverage product (preferably, a food or beverage product) and may be delivered in kit form, wherein the kit has the further advantage of disseminating information to the consumer regarding various health benefits and dose regimens of the compounds and compositions.

SUMMARY OF THE INVENTION

The present invention is directed to a compound having the structure:

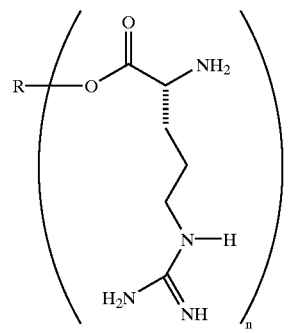

and acceptable salts, polypeptides, and pro-forms thereof, wherein R is selected from the group consisting of:
- (a) substituted glycerols; wherein n is an integer from 1 to 2;
- (b) vitamins; wherein n is 1;
- (c) sterols; wherein n is 1;
- (d) stanols; wherein n is 1;
- (e) $C_6$–$C_{32}$ alkyl; wherein n is 1; and
- (f) $C_6$–$C_{32}$ alkenyl; wherein n is 1.

The present invention is further directed to compositions and kits comprising these compounds as well as methods of using the compounds. The compounds, compositions, kits, and methods herein are useful for providing general health benefits to the consumer, particularly cardiovascular benefits, anti-menopausal benefits and/or treating sexual dysfunction (particularly, erectile dysfunction). Most particularly, the compounds, compositions, kits, and methods herein are useful for providing cardiovascular benefits, including lowering cholesterol in the consumer, treating, preventing, and/or inhibiting heart disease (e.g., atherosclerosis, restenosis, thrombosis) and, for example, treating other conditions such as hypercholesterolemia, hypertension, poor circulation, and complications associated with diabetes.

DETAILED DESCRIPTION OF THE INVENTION

The present invention is directed to compounds, and compositions comprising such compounds, which are useful for providing general health benefits to the consumer, particularly cardiovascular benefits, anti-menopausal benefits and/or treating sexual dysfunction (particularly, erectile dysfunction). The invention herein is further directed to kits comprising the compounds and compositions and methods of their use to provide the foregoing general health benefits.

Publications, patents, and patent applications are referred to throughout this disclosure. All references cited herein are hereby incorporated by reference.

All percentages and ratios are calculated by weight unless otherwise indicated. All percentages and ratios are calculated based on the total composition unless otherwise indicated.

All component or composition levels are in reference to the active level of that component or composition, and are exclusive of impurities, for example, residual solvents or by-products, which may be present in commercially available sources.

Referred to herein are trade names for components including, but not limited to, certain fats, flavors, and other components. The inventors herein do not intend to be limited by materials under a certain trade name. Equivalent materials (e.g., those obtained from a different source under a different name or catalog (reference) number) to those referenced by trade name may be substituted and utilized in the compositions, kits, and methods herein.

In the description of the invention various embodiments and/or individual features are disclosed. As will be apparent to the ordinarily skilled practitioner, all combinations of such embodiments and features are possible and can result in preferred executions of the present invention.

The compositions, methods, and kits herein may comprise, consist essentially of, or consist of any of the elements as described herein.

Definitions

As used herein, "alkyl" is an unsubstituted or substituted, branched or unbranched, saturated hydrocarbon radical. Unless otherwise specified herein, alkyls have from 1 to about 32 carbon atoms; preferably from about 3 to about 30 carbon atoms; more preferably from about 6 to about 28 carbon atoms; and most preferably from about 6 to about 22 carbon atoms.

As used herein, "alkenyl" is an unsubstituted or substituted, branched or unbranched hydrocarbon radical having at least one olefinic bond. Unless otherwise specified herein, alkenyls have from 2 to about 32 carbon atoms; preferably from about 3 to about 30 carbon atoms; more preferably from about 6 to about 28 carbon atoms; and most preferably from about 6 to about 22 carbon atoms. Preferred alkenyls are □-3-alkenyls having a double bond between carbon atoms 3 and 4 counting from the □ (distal) end of the alkenyl chain.

As used herein, "acylalkyl" is —C(O)-alkyl, wherein "C(O)" designates a carbon atom having a doubly bonded oxygen atom attached thereto.

As used herein, "acylalkenyl" is —C(O)-alkenyl, wherein "C(O)" designates a carbon atom having a doubly bonded oxygen atom attached thereto.

Compounds of the Present Invention

The present invention is directed to compounds which are useful for providing general health benefits to the consumer, particularly cardiovascular benefits, anti-menopausal benefits and/or treating sexual dysfunction (particularly, erectile dysfunction). The invention herein is further directed to compositions and kits comprising the compositions and methods of their use to provide the foregoing general health benefits. Most particularly, the compositions, kits, and methods herein are useful for providing cardiovascular benefits, including lowering cholesterol in the consumer, treating, preventing, and/or inhibiting heart disease (e.g., atherosclerosis, restenosis, thrombosis) and, for example, treating other conditions such as hypercholesterolemia, hypertension, poor circulation, and complications associated with diabetes.

The present compounds have the structure:

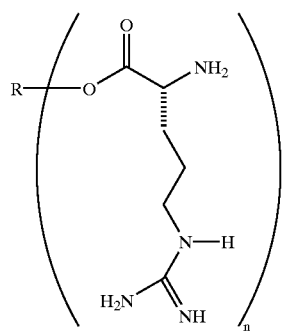

and acceptable salts, polypeptides, and pro-forms thereof, wherein R is selected from the group consisting of:

(a) substituted glycerols; wherein n is an integer from 1 to 2;
(b) vitamins; wherein n is 1;
(c) sterols; wherein n is 1;
(d) stanols; wherein n is 1;
(e) $C_6$–$C_{32}$ alkyl; wherein n is 1; and
(f) $C_6$–$C_{32}$ alkenyl; wherein n is 1.

For simplicity herein, the identical structure may be abbreviated as follows:

wherein, as used herein, it is understood that "Arg" represents L-arginine rather than the enantiomer D-arginine.

In discovering the present compounds, the present inventors have surprisingly found that the undesirable flavor of L-arginine is significantly diminished or removed through esterification with the components defined herein. Without intending to be limited by theory, the present inventors have excitingly discovered that by increasing the lipophilic nature of L-arginine, the unpalatable flavor associated with free L-arginine (and salts, polypeptides, and pro-forms) is removed and/or diminished. The present esters are further particularly useful for delivering cardiovascular and other health benefits associated with L-arginine. Additionally, the compounds herein have been carefully selected such that the in vivo hydrolysis products provide additional health benefits, for example, added nutritional supplementation or further cardiovascular benefit. These surprising and unexpected results allow for enhanced delivery and compliance associated with ingestion of L-arginine, while additionally providing the health benefits associated with the hydrolysis products.

As defined herein, L-arginine (including salts, polypeptides, and pro-forms thereof) may be esterified with a component selected from substituted glycerols, vitamins, sterols, stanols, $C_6$–$C_{32}$ alkyl, and $C_6$–$C_{32}$ alkenyl. Each of these components is more particularly described below.

L-Arginine

L-arginine and its salts, polypeptides, and pro-forms, schematically represented as a critical element of the above structure, is commonly known in the art. L-arginine is a natural amino acid which has been identified to provide certain general health benefits including, for example, cardiovascular benefits, including lowering cholesterol in the consumer, and treating, preventing, and/or inhibiting heart disease (e.g., atherosclerosis, restenosis, hypertension, poor circulation, and/or complications associated with diabetes. See e.g., Moskowitz, U.S. Pat. No. 5,385,940, assigned to The General Hospital Corp., issued Jan. 31, 1995; Sonaka et al., EP 0,546,796, assigned to Ajinomoto Co., published Jun. 16, 1993; Cotter et al., U.S. Pat. No. 4,920,098, assigned to Baxter International Inc., issued Apr. 24, 1990; Dudrick, U.S. Pat. No. 5,032,608, issued Jul. 16, 1991; Levere et al., U.S. Pat. No. 5,217,997, issued Jun. 8, 1993; Cooke et al., U.S. Pat. No. 5,428,070, assigned to Stanford University, issued Jun. 27, 1995; Chibata et al., U.S. Pat. No. 4,420,432, assigned to Tanabe Seiyaky Co., issued Dec. 13, 1983; Varma et al., U.S. Pat. No. 5,364,884, assigned to Baylor College of Medicine, issued Nov. 15, 1994; and Barbul, U.S. Pat. No. 5,157,022, issued Oct. 20, 1992.

The L-arginine utilized herein may be used in its free form or may be utilized as a polypeptide, a salt, and/or a pro-form. Preferably, the L-arginine is utilized in its free form or as a salt. The salt used herein should be an acceptable salt, i.e., a salt useful in pharmaceutical and/or food compositions, preferably food compositions. Because the L-arginine herein is esterified at the carboxylic acid site, the L-arginine salts herein will be anionic salts, i.e., salts formed at any basic (e.g., amino) group. Salts of L-arginine are well-known in the art. For example, organic salts such as phosphate, citrate, acetate, malate, tartrate, fumarate, adipate, and lactate, as well as inorganic salts such as hydrochloride and hydrobromide may be utilized.

Polypeptides of L-arginine are also well-known in the art. Preferred polypeptides for use herein include those which are readily hydrolyzed in vivo to provide free L-arginine, or the L-arginine esterified as defined herein. Dipeptides and tripeptides of L-arginine are particularly preferred.

Pro-forms of L-arginine may also be utilized herein Pro-forms (also commonly referred to as pro-drugs) are those forms which, upon hydrolysis in vivo, provide the free L-arginine. Non-limiting, but preferred, examples of such pro-forms include amides of L-arginine, particularly amides of the α-nitrogen of L-arginine. For example, methyl, ethyl, propyl, and butyl amides are preferred pro-forms herein.

As described further herein, the L-arginine is actually an ester of a moiety designated herein as "R" which is a glycerol backbone, a substituted glycerol backbone, a vitamin, a sterol, a stanol, $C_6$–$C_{32}$ alkyl, or $C_6$–$C_{32}$ alkenyl. As will be further described, in some instances, more than one molecule of L-arginine (or salt, polypeptide, or pro-form) may be attached to the substituted glycerol backbone. The R moieties are further described below.

Substituted Glycerols

The compound of the present invention may be an ester of a substituted glycerol backbone (described herein for simplicity as substituted glycerol) and L-arginine, or acceptable salts, polypeptides, and pro-forms thereof. The compound may be either mono-substituted or di-substituted with a moiety other than L-arginine or the normally occurring hydroxyl moiety. Thus, wherein the compound is mono-substituted, two L-arginine molecules are esterified and n is 2, or one L-arginine molecule is esterified and one free hydroxyl moiety is present on the substituted glycerol. Similarly. wherein the compound is di-substituted, one L-arginine molecule is esterified and n is 1. Preferably, wherein R is a substituted glycerol, the substituted glycerol is di-substituted.

As used herein, the term "substituted" means that one or more hydroxy moieties on the glycerol backbone is substituted with a moiety independently selected from alkyl, alkenyl, acylalkyl, and acylalkenyl. Preferably, one or more hydroxy moieties on the glycerol backbone are substituted with a moiety independently selected from acylalkyl and acylalkenyl, most preferably acylalkenyl. Such alkyl, alkenyl, acylalkyl, or acylalkenyl may be further substituted with a substituent selected from alkyl, alkenyl, alkoxy (i.e., —O-alkyl or —O-alkenyl), hydroxy, oxo (C(O)), nitro, amino, cyano, halo, carboxy, acylalkyl, acylalkenyl, thiol, imino, thioxo (C(S)), preferably alkyl, alkoxy, hydroxy, oxo, nitro, amino, halo, and thiol, more preferably alkyl, alkoxy, hydroxy, oxo, nitro, amino, and halo, even more preferably alkyl, alkenyl, and alkoxy.

For example, the substituted glycerol may be a di-substituted glycerol (n is 1) wherein two hydroxy moieties of the glycerol backbone are independently substituted with an acylalkyl. To illustrate, such compound has the structure:

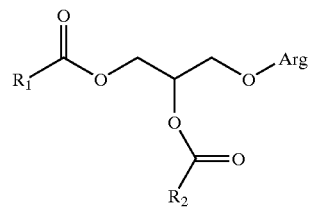

wherein $R_1$ and $R_2$ are each, independently, alkyl.

Wherein the glycerol backbone is substituted with a moiety selected from acylalkyls and acylalkenyls, it is preferred that such moieties are derived from readily available fatty acids, preferably those which are suitable for use in food and beverage compositions. Such fatty acids include, but are not limited to, $C_6$ fatty acid, $C_8$ fatty acid, $C_{10}$ fatty acid, $C_{12}$ fatty acid (e.g., laurate), $C_{14}$ fatty acid (e.g., myristate), $C_{16}$ fatty acid (e.g., palmitate and palmitoleate), $C_{18}$ fatty acid (e.g., stearate, oleate, linoleate, and linolenate), $C_{20}$ fatty acid (e.g., arachidate and arachidonate), $C_{22}$ fatty acid (e.g., behenate), and $C_{24}$ fatty acid (e.g., lignocerate).

In a particularly preferred embodiment, one or two (preferably, two) hydroxy moieties on the glycerol backbone are independently substituted with an acylalkenyl moiety, such as one derived from the above fatty acids and having at least one olefinic bond. Preferred acylalkenyls are those which are derived from □-3-fatty acids. As is known in the art, □-3-fatty acids are those fatty acids which have an olefinic bond bridging carbon atoms 3 and 4, wherein the carbon atoms of the fatty acid chain are counted from the □ (distal) end of the fatty acid. Therefore, as used herein, a particularly preferred embodiment is wherein one or more hydroxy moieties on the glycerol backbone are substituted with an □-3-acylalkenyl. To illustrate, such compounds may have the following non-limiting structure:

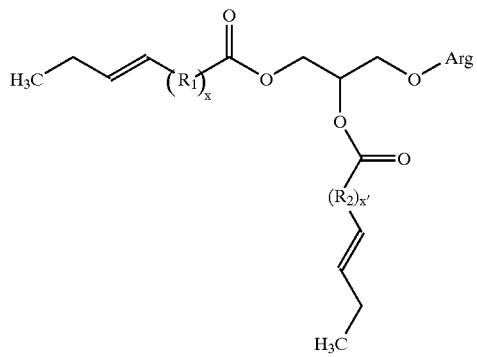

wherein $R_1$ and $R_2$ are each, —$CH_2$—; and wherein x and x' are independent integers typically from about 3 to about 33. Alternatively, as another non-limiting example, the □-3-fatty acid chains may comprise one or more additional olefinic bonds.

Vitamins

The compounds of the present invention may also be an ester of a vitamin and L-arginine, or salts, pre-forms, or polypeptides thereof. In this embodiment of the present invention, the integer n will be 1. Preferably, the vitamin utilized bears at least one hydroxy moiety, making the vitamin readily available for esterification.

Utilization of a vitamin herein provides not only reduction or removal of unacceptable flavor of the L-arginine, but also provides an additional nutritional benefit imparted by such vitamin. Since ingestion and absorption of the present compounds will result in in vivo hydrolysis of the ester functionality, the vitamin utilized will be released, providing the nutritional benefit of such vitamin. Nutritional benefits of the various vitamins are well-known in the art. Accordingly, utilization of a vitamin for the R moiety of the present ester compounds is a particularly preferred embodiment of the present invention.

The vitamin utilized herein should be one which comprises a hydroxy moiety, thus making such vitamin suitable for esterification with L-arginine. Non-limiting examples of such vitamins include vitamin A, vitamin D, vitamin E, and vitamin $K_5$. Additionally, the present inventors have discovered that the fat-soluble vitamins, e.g., vitamin A, vitamin D, and vitamin E, are most preferred herein due to their lipophilicity. As discovered herein, wherein the L-arginine is made more lipophilic, the adverse flavor of the L-arginine is diminished and/or removed more readily. Accordingly, while any vitamin bearing a hydroxy moiety may be utilized, it is preferred that R is selected from vitamin A, vitamin D, and vitamin E. The most preferred vitamin for use as R is vitamin E.

As used herein, all forms of these vitamins are contemplated for use. For example, vitamin D can include vitamin $D_1$, $D_2$, $D_3$, and $D_4$. Similarly, vitamin A can include vitamin A and $A_2$. Preferably, wherein vitamin A is used, such vitamin A is in the form of retinol. Also preferably, wherein vitamin E is utilized, such vitamin E is a tocopherol (e.g., α-tocopherol, β-tocopherol γ-tocopherol, and δ-tocopherol, preferably α-tocopherol) or a tocotrienol (e.g., α-tocotrienol, β-tocotrienol, γ-tocotrienol, and δ-tocotrienol. Most preferably, such vitamin E is α-tocopherol.

Non-limiting examples of preferred compounds wherein R is a vitamin are set forth in Table 1 below. If desired, these compounds may be modified as their acceptable salts, polypeptides, and pro-forms.

TABLE 1

Non-limiting Examples of Compounds Wherein R is a Vitamin

| R | Compound |
|---|---|
| Vitamin A |  |

TABLE 1-continued
Non-limiting Examples of Compounds Wherein R is a Vitamin
| R | Compound |
|---|---|
| Vitamin A$_2$ | 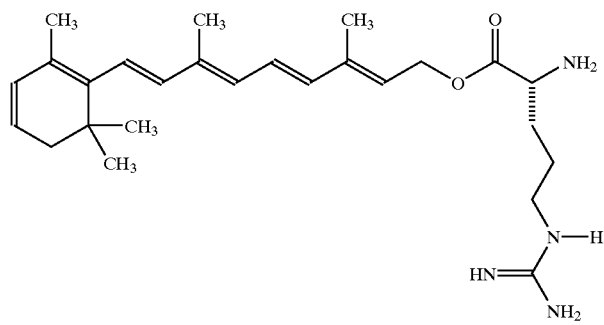 |
| Vitamin D$_2$ | 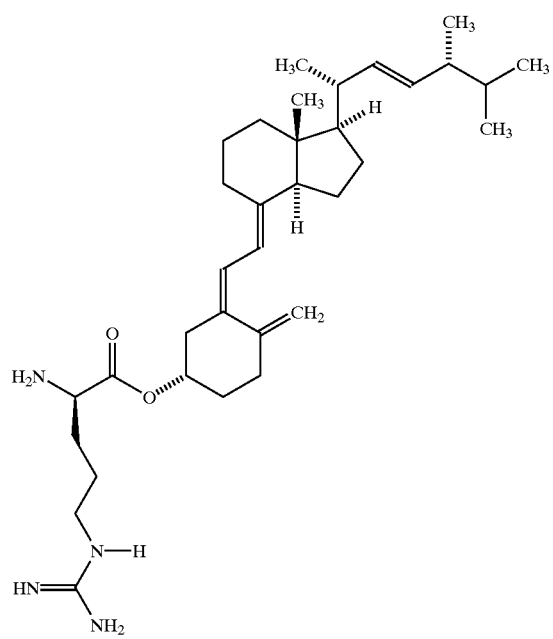 |
| Vitamin D$_3$ | 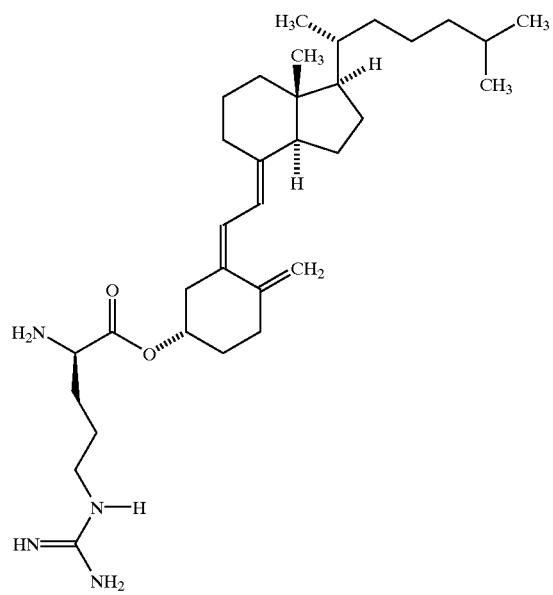 |

TABLE 1-continued

Non-limiting Examples of Compounds Wherein R is a Vitamin

| R | Compound |
|---|---|
| Vitamin $D_4$ | 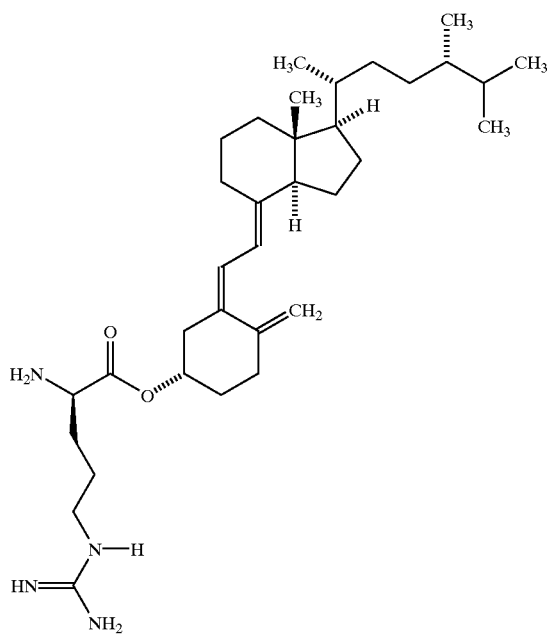 |
| Vitamin E | 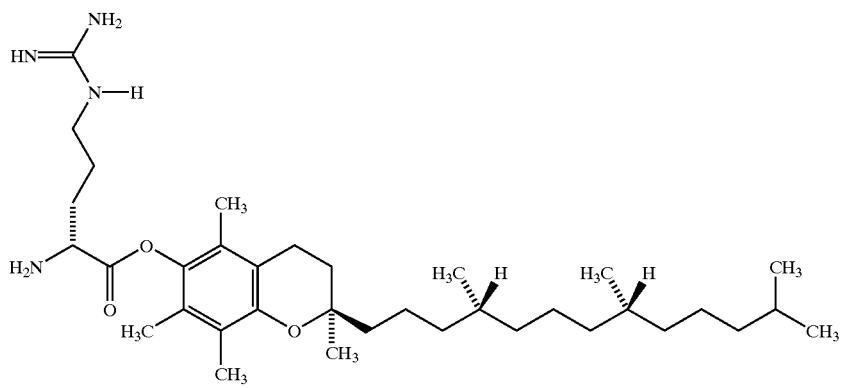 |

Sterols

The compound of the present invention may also be an ester of L-arginine and a sterol. In this embodiment of the present invention, the integer n will be 1.

Utilization of a sterol herein provides not only reduction or removal of unacceptable flavor of the L-arginine, but also provides an additional cardiovascular benefit imparted by such sterol. Since ingestion and absorption of the present compounds will result in in vivo hydrolysis of the ester functionality, the sterol utilized will be released, providing the cardiovascular benefit of such sterol. As has recently been discovered, sterols may be utilized in food compositions to enhance cardiovascular health, for example, by decreasing serum cholesterol levels. Accordingly, use of such sterols surprisingly improves the flavor of L-arginine, while providing additional health benefits to the consumer.

Sterols which are useful herein are commonly known in the art. As non-limiting examples, such sterols are described in Stern, U.S. Pat. No. 3,004,043, assigned to Eastman Kodak Co., issued Oct. 10, 1961; Wruble et al., U.S. Pat. No. 3,085,939, issued Apr. 1, 1963; Erickson, U.S. Pat. No. 3,751,569, assigned to The Procter & Gamble Co., issued Aug. 7, 1973; Jandacek, U.S. Pat. No. 3,865,939, assigned to The Procter & Gamble Co., issued Feb. 11, 1975; Ong, U.S. Pat. No. 4,195,084, assigned to Eli Lilly and Co., issued Mar. 25, 1980; Malinow, U.S. Pat. No. 4,461,762, assigned to Medical Research Foundation, issued Jul. 24, 1984; Arichi et al., U.S. Pat. No. 4,524,067, assigned to Osaka Chemical Lab. Co., issued Jun. 18, 1985; Malinow, U.S. Pat. No. 4,602,003, assigned to Medical Research Foundation, issued Jul. 22, 1986; Cassal, U.S. Pat. No. 4,680,290, assigned to Hoffman-La Roche Inc., issued Jul. 14, 1987; Ambrus et al., U.S. Pat. No. 5,112,815, issued May 12, 1992; Straub, U.S. Pat. No. 5,244,887, issued Sep. 14, 1993; Eugster et al., U.S. Pat. No. 5,270,041, assigned to Marigen S. A., issued Dec. 14, 1993; Mazur et al., U.S. Pat. No. 5,591,836, assigned to The Procter & Gamble Co., issued Jan. 7, 1997; Moreau et al., U.S. Pat. No. 5,843,499, assigned to United States of America, issued Dec. 1, 1998; Miettenen et al., U.S. Pat. No. 5,958,913, assigned to Raisio Benecol Ltd., issued Sep. 28, 1999; Karppanen et al., WO 98/28990, assigned to Pharmaconsult, published Jul. 9, 1998; Shirakawa et al., EP 0,289,636, published Nov. 9, 1988; Ko, WO 94/18225, assigned to Du Pont Merck Pharmaceutical, published Aug. 18, 1994; Festo, WO 95/08342, assigned to Inpharma S. A., published Mar. 30, 1995; Ritter et al., WO 97/42830, assigned to Unilever PLC, published Nov. 20, 1997; Van Amerongen et al., WO 98/01126, assigned to Unilever PLC, published Jan. 15, 1998; and Wester et al., WO 98/06405, assigned to Raision Tehtaat, published Feb. 19, 1998. Any of the sterols described in the foregoing references, as well as those commonly known in the art, may be utilized for the R moiety of the present compounds.

Thus, the term "sterol" as used herein can include natural or synthetic plant or animal sterols or triterpenes. This includes the phytosterols and the mycosterols as well as cholesterol, however it is preferred herein that cholesterol itself is not utilized. For a more detailed discussion of sterols see, for example, Nes, W. D., Parish, E .J., Eds., "Analysis of Sterols and Other Biologically Significant Steroids", Academic Press, Inc. (1989). Non-limiting examples of preferred sterols include diosgenin, stigmastanol, tigogenin, □-sitosterol, □-sitosterol, stigmasterol, ergosterol, campesterol, oleanoic acids, soyasapogenols, protoascigenin, togenols, protoparaxadiols, protopanaxadiols, □-amyrin, □-amyrin, lupeol, butyrospermol, germanicol, 4-desmethylsterols, 4-monomethylsterols, and 4,4'-dimethylsterols. Other non-limiting examples of sterols for use herein include 7-dehydrocholesterol, 22-dehydrocholesterol, 24-dehydrocholesterol, zymosterol. Δ⁷-cholesterol, cerebrosterol, 22-α-oxycholesterol, 22-dihydroerogosterol, neospongosterol, cerebisterol, corbisterol, focosterol, α-spinasterol, sargasterol, 7-dehydrocryonasterol, poriferasterol, chondrillasterol, cryonasterol (γ-sitosterol), dihydro-γ-sitosterol, 14-dehydroergosterol, 24(28)-dehydroergosterol, ergosterol, brassicasterol, 24-methylenecholesterol, ascosterol, episterol, fecosterol, and 5-dihydroergosterol.

It is particularly preferred herein that phytosterols are utilized herein. The term phytosterol is intended to mean unsaturated sterol alcohols and their mixtures derived from plants, as well as synthetically produced sterol alcohols and their mixtures which are either identical to those sterols found in nature, or having properties which am similar to those of naturally occurring sterols. As is well-known in the art, phytosterols (also commonly referred to as plant sterols) are, natural components of, for example, vegetable fats and oils.

The most preferred phytosterols for use as the R moiety herein include sitosterols (e.g., β-sitosterol (24-ethyl-5-α-cholestane-3β-ol and 5α-sitosterols), stigmasterol, and campesterol. Schematic drawings of these components are as given in S. P. Kochhar, "Influence of Processing on Sterols of Edible Vegetable Oils", Prog. Lipid Res., Vol. 22, pp. 161–188. For example, β-sitosterol has the following structure:

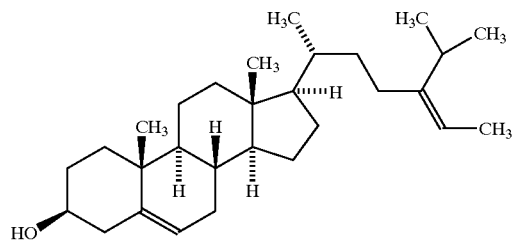

Accordingly, as a non-limiting example, where R is β-sitosterol, a compound of the present invention has the structure:

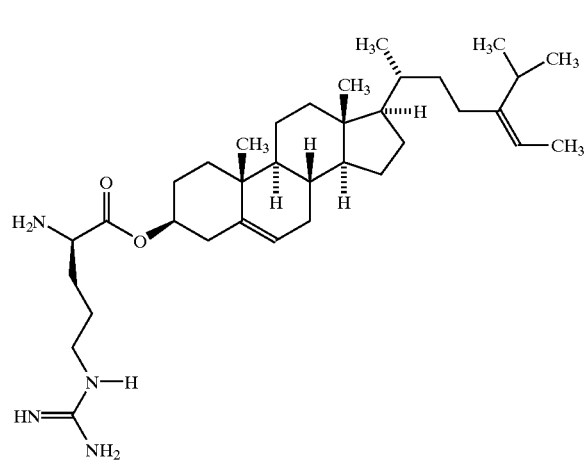

Preparation of phytosterols is commonly known; for example, sitosterol can be obtained from wood and from refining vegetable oil, and normally comprises a minor amount of other sterols, such as campesterol, stigmasterol, and various avenasterols. Other suitable phytosterols for use herein include brassicasterol and 22,23-dihydrobrassicasterol.

Stanols

The compound of the present invention may also be an ester of L-arginine and a stanol. In this embodiment of the present invention, the integer n will be 1.

As with utilization of a sterol, the stanol herein provides not only reduction or removal of unacceptable flavor of the L-arginine, but also provides an additional cardiovascular benefit imparted by such stanol. The stanol utilized will be released upon in vivo hydrolysis, providing the cardiovascular benefit of such stanol. As has recently been discovered, stanols may be utilized in food compositions to enhance cardiovascular health, for example, by decreasing serum cholesterol levels. Accordingly, use of such stanols surprisingly improves the flavor of L-arginine, while providing additional health benefits to the consumer.

Stanols are found in small amounts in nature in such products as wheat, rye, corn, and triticale. They can also easily be produced by hydrogenation of natural sterol mixtures such as vegetable oil-based sterol mixtures or commercially available wood sterols. The plant sterols thus obtained can be converted into stanols by well-known hydrogenation techniques such as those based on the use of a Pd/C catalyst (or other similar catalyst) in organic solvent. A wide variety of palladium catalysts and solvents are known to those of ordinary skill in the art and such catalysis can be used to hydrogenate the sterol for formation of the desired stanol. For example, β-sitostanol (24-ethyl-5α- cholestane-3β-ol) may be prepared by hydrogenation of β-sitosterol in organic solvent.

Accordingly, any sterol, including the foregoing examples of sterols, may be utilized to provide the desired stanol. Non-limiting examples of useful stanols therefore include the hydrogenation products of the sterols described herein. The most preferred stanols herein include stanols of the phytosterols, for example, sitostanols (e.g., β-sitostanol and 5α-sitostanols), campestanol, 24-β-methyl cholestanol, stiginastanol, clionastanol, and dihydrobrassicastanol, which may be described herein as phytostanols. For example, four major phytostanols are campestanol, 22,23-dihydrobrassicastanol, β-sitostanol, and clionastanol, which have the following structure:

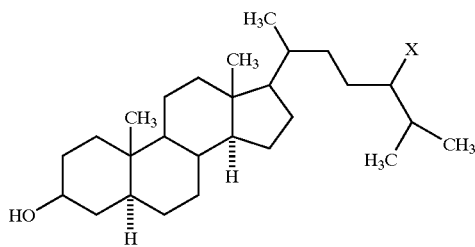

wherein X is —CH$_3$ for campestanol and its epimer, 22,23-dihydrobrassicastanol and wherein X is —C$_2$H$_5$ for sitostanol and its epimer, clionastanol. Campestanol and 22,23-dihydrobrassicastanol differ only by their steric configuration at C$_{24}$. Similarly, sitostanol and clionastanol differ only by their steric configuration at C$_{24}$. Alternate nomenclature for clionastanol is (3β, 5α, 24S)-stigmast-5an-3-ol; sitostanol is (3β, 5α, 24R)-stigmast-5an-3-ol; campestanol is (3β, 5α, 24R)-ergost-5an-3-ol; dihydrobrassicastanol is (3β, 5α, 24S)-ergost-5an-3-ol.

Non-limiting examples of compounds which may be utilized herein and having R as a stanol therefore include those of the following structure:

wherein X is as described above for the major phytostanols.

C$_6$–C$_{32}$ Alkyl and Alkenyl

The compounds suitable for use herein may also be esters of a C$_6$–C$_{32}$ alkyl or C$_6$–C$_{32}$ alkenyl and L-arginine, or salts, polypeptides, or pro-forms thereof. In this embodiment, the integer n will be 1.

It has been discovered that use of the present alkyls and alkenyls as esters of L-arginine significantly increases the lipophilicity of L-arginine which, in turn, surprisingly improves the flavor of L-arginine such that it is palatable and acceptable for use. Accordingly, compounds wherein the R moiety is C$_6$–C$_{32}$ alkyl or C$_6$–C$_{32}$ alkenyl are particularly preferred herein. Preferably, in this embodiment, R is C$_{10}$–C$_{28}$ alkyl or alkenyl, more preferably C$_{12}$–C$_{22}$ alkyl or alkenyl, and most preferably C$_{16}$–C$_{22}$ alkyl or alkenyl.

Fatty alcohols may be utilized for esterification to provide the present ester compounds. For example, preferred alcohols include hexyl, octyl, decyl, lauryl, myristyl, cetyl, and stearyl alcohol. The most preferred alcohols for use herein are those which are suitable for use in foods and beverages.

Non-limiting examples of compounds wherein R is C$_6$–C$_{32}$ alkyl are set forth below in Table 2.

TABLE 2

| R | Compound |
|---|---|
| C$_6$ alkyl | |
| C$_8$ alkyl | |
| C$_{10}$ alkyl | |

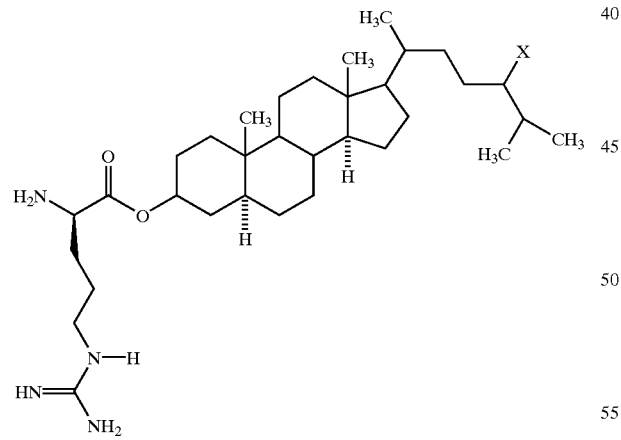

TABLE 2-continued
| R | Compound |
|---|---|
| C₁₂ alkyl | 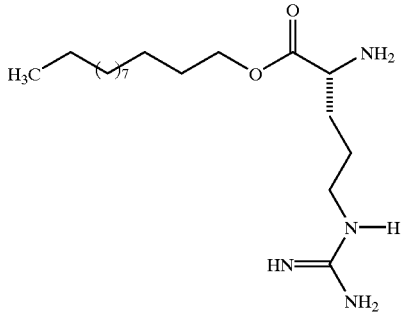 |
| C₁₄ alkyl | 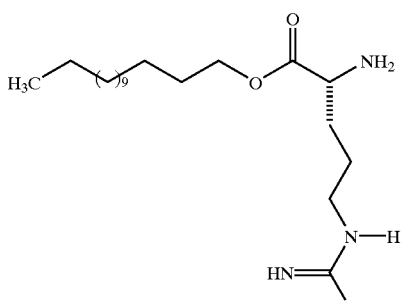 |
| C₁₆ alkyl | 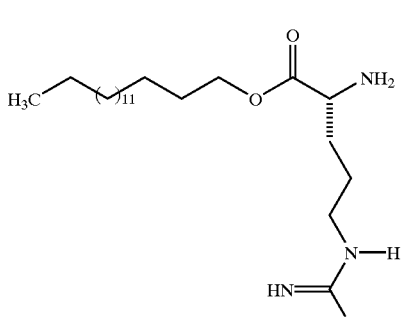 |
| C₁₈ alkyl | 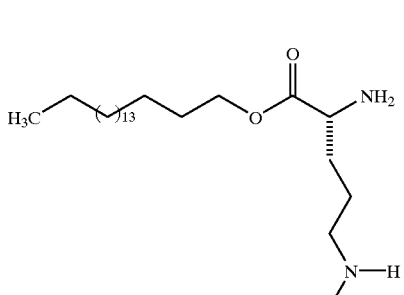 |
| C₂₀ alkyl | 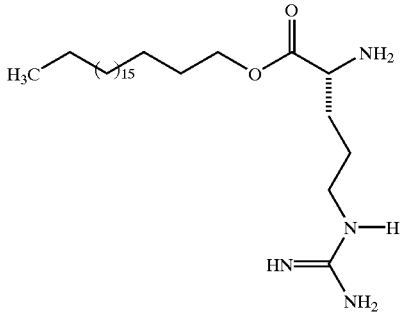 |
| C₂₂ alkyl | 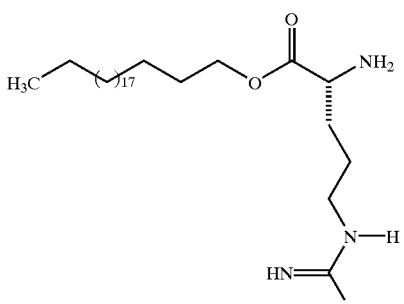 |
| C₂₄ alkyl | 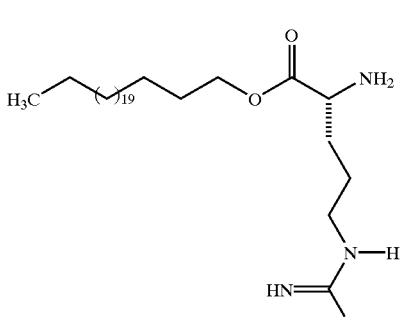 |
| C₂₆ alkyl | 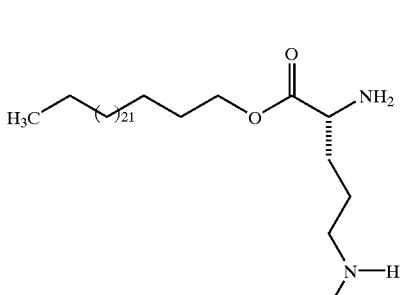 |

TABLE 2-continued

| R | Compound |
|---|---|
| $C_{28}$ alkyl | $H_3C-(\phantom{x})_{23}$—O—C(=O)—CH(NH$_2$)—CH$_2$CH$_2$CH$_2$—NH—C(=NH)—NH$_2$ |
| $C_{30}$ alkyl | $H_3C-(\phantom{x})_{25}$—O—C(=O)—CH(NH$_2$)—CH$_2$CH$_2$CH$_2$—NH—C(=NH)—NH$_2$ |
| $C_{32}$ alkyl | $H_3C-(\phantom{x})_{27}$—O—C(=O)—CH(NH$_2$)—CH$_2$CH$_2$CH$_2$—NH—C(=NH)—NH$_2$ |

Alkenyls of the compounds set forth in Table 2 are also particularly useful. For example, ω-3 alkenyls, i.e., those which have an olefinic bond between carbon atoms 3 and 4 of the ω (distal) end of the carbon chain are preferred embodiments herein. For example, wherein R is an ω-3 $C_8$ alkenyl the corresponding L-arginine ester has the following structure:

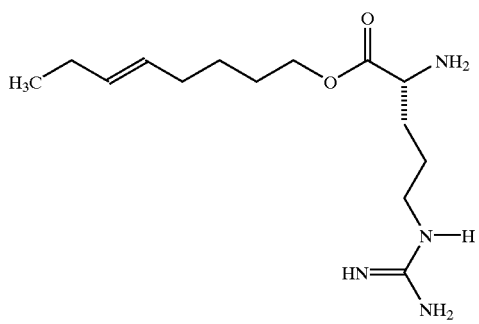

Kits of the Present invention

The present invention further relates to kits comprising a compound as described herein, or a composition comprising such compound, and information that use of the compound/composition provides treatment against general health benefits. Such general health benefits include, but are not limited to, cardiovascular benefits, including lowering cholesterol in the consumer, treating, preventing, and/or inhibiting heart disease (e.g, atherosclerosis, restenosis, thrombosis) and, for example, treating other cardiovascular conditions such as hypercholesterolemia, hypertension, poor circulation, and other complications associated with diabetes. Additionally, the kit may comprise information that use of the compound/composition provides an organoleptic benefit, for example acceptable (e.g., good) flavor.

The information provided within the kit may for example, be oral information disseminated as part of the kit, but is preferably written information. Such written information is typically present on packaging associated with the composition (e.g., a label present on a package containing the compound/composition or package insert included within the kit). As used herein, "written" means through words, pictures, symbols, and/or other visible information. Such information need not utilize the actual words but rather use of pictures, symbols, and the like conveying the same or similar meaning are contemplated within the scope of this invention. Such information may also include information about general health benefits and reasons for which such health, and particularly treatment against certain disease states (including the aforementioned disease states), is important for the user.

Methods of the Present Invention

The present invention also encompasses methods for providing certain health benefits, particularly, lowering serum cholesterol or treating other cardiovascular problems or diseases (as set forth herein) comprising systemically (generally, orally) administering to a mammal (preferably, a human) successive therapeutically effective doses of the present compositions. Such methods include treating, preventing, and/or inhibiting (collectively referred to herein as treating) one or more of the following: cardiovascular problems including, but not limited to, atherosclerosis, restenosis, thrombosis, hypercholesterolemia, hypertension, diabetes, vascular dysfunction, and poor circulation, and other problems such as shock. Preferred methods herein include treatment of one or more of atherosclerosis, hypercholesterolemia, hypertension, diabetes, and poor circulation.

In accordance with the methods of the present invention, a present compound or, preferably a composition comprising the compound, is administered to a mammal, preferably a human. Preferably such administration is oral. As used herein, the term "oral administration" (or the like) with respect to the mammal (preferably, human) means that the mammal ingests or is directed to ingest (preferably, for the purpose of treatment of one or more of the various health problems described herein) one or more compounds/compositions of the present invention. Wherein the mammal is directed to ingest one or more of the compounds/compositions, such direction may be that which instructs and/or informs the user that use of the composition may and/or will provide treatment for the particular health problem of concern. For example, such direction may be oral direction (e.g., through oral instruction from, for example, a physician, sales professional or organization, and/or radio or television media (i.e., advertisement) or written direction (e.g., through written direction from, for example, a physician or other medical professional (e.g., scripts), sales professional or organization (e.g., through, for example, marketing brochures, pamphlets, or other instructive paraphernalia), written media (e.g., internet, electronic mail, or other computer-related media), and/or packaging associated with the composition (e.g., a label present on a package containing the composition). As used herein, "written" means through words, pictures, symbols, and/or other visible descriptors.

Administration of the present compounds/compositions may be via any systemic method, however, such administration is preferably oral. Typically such administration is at least once monthly, but preferably weekly, and most preferably daily. Preferred dosages of the present compounds/compositions will vary. As one of ordinary skill will recognize such variations are largely dependent upon factors such as age, gender, weight, and health state of the consumer. However, it is often preferred that from about 0.05 grams to about 200 grams of the compound is administered daily either alone or in such composition. More preferably, from about 0.01 grams to about 20 grams, even more preferably from about 0.1 gram to about 45 grams, and most preferably from about 0.5 grams to about 27 grams of the compound is administered daily either alone or in such composition.

Methods of Making

The compounds of the present invention are prepared according to methods which are well-known to those skilled in the art. The starting materials used in preparing the compounds of the invention are known, made by known methods, or are commercially available as a starting material.

It is recognized that the ordinarily skilled artisan in the art of organic chemistry can readily carry out standard manipulations of organic compounds without further direction. Examples of such manipulations are discussed in standard texts such as J. March, *Advanced Organic Chemistry*, John Wiley & Sons, 1992.

The skilled artisan will readily appreciate that certain reactions are best carried out when other functionalities are masked or protected in the compound, thus increasing the yield of the reaction and/or avoiding any undesirable side reactions. Often, the skilled artisan utilizes protecting groups to accomplish such increased yields or to avoid the undesired reactions. These reactions are found in the literature and are also well within the scope of the skilled artisan. Examples of many such manipulations can be found in, for example, T. Greene, *Protecting Groups in Organic Synthesis*, John Wiley & Sons, 1981.

The compounds of the present invention may have at least one chiral center (due to the use of L-arginine herein). As a result, one may selectively prepare one optical isomer, including diastereomers and enantiomers, over another, for example by chiral starting materials, catalysts or solvents, or may prepare both stereoisomers or both optical isomers, including diastereomers and enantiomers at once (a racemic mixture). Mixtures of optical isomers, including diastereomers, enantiomers, or stereoisomers may be separated using known methods, such as through the use of, for example, chiral salts and chiral chromatography.

As stated, the present compounds are made according to procedures which are well-known to the ordinarily skilled artisan. However, for convenience, as a general procedure, L-arginine and a second reactant (selected according to the desired final compound herein, for example, a sterol, vitamin, etc.), are combined along with an inert solvent system to facilitate the solubilization of both reactants. The reaction mixture is heated to a temperature below the decomposition temperature of the L-arginine. A base catalyst (along with a non-reactive emulsifier, if necessary) is added. The reaction in maintained under slight vacuum to remove any moisture generated during the reaction. Solvent is refluxed back into the reactor. Upon completion of the reaction, the reaction mixture is neutralized and the excess reactants are removed. The desired compound may be extracted and further purified using silica gel (or other chromatographic methods).

Use of the Present Compositions and Kits

The compounds described herein can be used in compositions comprising fat and non-fat components to provide general health benefits, including cardiovascular benefits, such as lowering cholesterol in the consumer, treating, preventing, and/or inhibiting heart disease (e.g., atherosclerosis, restenosis, thrombosis) and, for example, treating other conditions such as hypertension, poor circulation, and complications associated with diabetes. The compositions are useful in a wide variety of finished products, including pharmaceutical, food, and beverage products.

Preferred herein is use of the present compositions in food products, including those envisioned for use as a dietary supplement such as a health bar. In a preferred embodiment of the present invention, the compositions is in the form of a health bar.

As non-limiting examples, the compounds can be used in the production of baked goods in any form, such as mixes, shelf-stable baked goods (including health bars), and frozen baked goods. Applications include, but are not limited to, cakes, brownies, muffins, bar cookies, health bars, wafers, biscuits, pastries, pies, pie crusts, and cookies, including sandwich cookies and chocolate chip cookies, particularly the storage-stable dual-textured cookies described in Hong et al., U.S. Pat. No. 4,455,333. The baked goods can contain fruit, cream, or other fillings. Other baked good uses include breads and rolls, crackers, pretzels, pancakes, waffles, ice cream cones and cups, yeast-raised baked goods, pizzas and pizza crusts, baked farinaceous snack foods, and other baked salted snacks.

As stated, health bars are a particularly preferred embodiment of the present invention. The compounds can be incorporated into health bars, such as those described in Greenberg et al., U.S. Pat. No. 5,780,039. The foregoing doses of the present compounds may be included in the advantageous health bars according to the present invention.

In addition to their uses in baked goods, the compositions herein can be used alone or in combination with fats to make shortening and oil products. The fats can be synthetic or derived from animal or vegetable sources, or combinations of these. Shortening and oil products include, but are not limited to, shortenings, margarines, spreads, butter blends, lards, cooking and frying oils, salad oils, popcorn oils, salad dressings, mayonnaise, and other edible oil products. In a particular embodiment of the present invention, the compositions are selected from margarines, butter, dressings and spreads.

Other uses for the compositions of the present invention include partial or complete replacement fats and/or oils present in peanut butter, frozen desserts such as ice cream and ice cream coatings, whipped toppings, frosting products, processed meat products, including vegetable protein-based meat analog products, sauces, gravies, and dairy products such as milkshakes, milk products, coffee whiteners, and cheese products.

The compounds described herein are also particularly useful in beverage compositions. Such beverage compositions may be "near-water" beverages (slightly flavored water), milks, coffees, teas, colas, fortified beverages (e.g., calcium fortified beverage), and fruit juices.

Preferred beverage compositions of the present invention are those comprising a beverage member selected from the group consisting of water, fruit juice, tea solids, milk solids, fruit flavors, botanical flavors, and mixtures thereof. The beverage compositions herein are most preferably dilute juice beverages (particularly fruit juice beverages) and beverages containing tea solids, and beverage products comprising fruit juice and tea solids. Particularly preferred beverage products comprise both fruit juice and water. Other particularly preferred beverage products comprise both tea solids and water. In another preferred embodiment, "near water" (lightly flavored water) is utilized.

Various optional elements may be incorporated into the compositions and kits of the present invention. Non-limiting examples of optional elements are as follows:

Water

Water may be included in the compositions of the present invention, particularly wherein the compositions are beverage compositions. As used herein, the term "water" includes the total amount of water present in the composition. "Water" includes water from flavor agents, sugar syrups, and other sources, e.g., gum solutions. Water of hydration of, for example, calcium and other solids, is also included. Wherein water is included, water is preferably included at levels from about 0.1% to about 99.999%, more preferably from about 5% to about 99%, still more preferably from about 40% to about 95%, even more preferably from about 50% to about 90%, and most preferably from about 70% to about 90%, by weight of the composition.

Beverage Emulsions

Dilute juice beverages of the present invention may optionally, but preferably, comprise from about 0.2% to about 5%, preferably from about 0.5% to about 3%, and most preferably from about 0.8% to about 2%, of a beverage emulsion. This beverage emulsion can be either a cloud emulsion or a flavor emulsion.

For cloud emulsions, the clouding agent can comprise one or more fats or oils stabilized as an oil-in-water emulsion using a suitable food grade emulsifier. Any of a variety of fats or oils may be employed as the clouding agent, provided that the fat or oil is suitable for use in foods and/or beverages. Preferred are those fats and oils that have been refined, bleached and deodorized to remove off-flavors. Especially suitable for use as clouding agents are those fats that are organoleptically neutral. These include fats from the following sources: vegetable fats such as soybean, corn, safflower, sunflower, cottonseed, canola, and rapeseed; nut fats such as coconut, palm, and palm kernel; and synthetic fats. See e.g., Kupper et al., U.S. Pat. No. 4,705,691, issued Nov. 10, 1987, for suitable fat or oil clouding agents.

Any suitable food grade emulsifier can be used that can stabilize the fat or oil clouding agent as an oil-in-water emulsion. Suitable emulsifiers include gum acacia, modified food starches (e.g., alkenylsuccinate modified food starches), anionic polymers derived from cellulose (e.g., carboxymethylcellulose), gum ghatti, modified gum ghatti, xanthan gum, tragacanth gum, guar gum, locust bean gum, pectin, and mixtures thereof. See e.g., Kupper et al., U.S. Pat. No. 4,705,691, issued Nov. 10, 1987. Modified starches treated to contain hydrophobic as well as hydrophilic groups, such as those described in Caldwell et al., U.S. Pat. No. 2,661,349, are preferred emulsifiers for use as herein. Octenyl succinate (OCS) modified starches such as those described in Marotta et al., U.S. Pat. No. 3,455,838 and Barndt et al., U.S. Pat. No. 4,460,617 are especially preferred emulsifiers.

The clouding agent can be combined with a weighting agent to provide a beverage opacifier that imparts a total or partial opaque effect to the beverage without separating out and rising to the top. The beverage opacifier provides the appearance to the consumer of a juice-containing beverage. Any suitable weighting oil can be employed in the beverage opacifier. Typical weighting oils include brominated vegetable oil, glycerol ester of wood rosin (ester gum), sucrose acetate isobutyrate (SAIB) and other sucrose esters, gum damar, colophony, gum elemi, or others known to those skilled in the art. Other suitable weighting agents include brominated liquid polyol polyesters which are nondigestible. See e.g., Brand et al., U.S. Pat. No. 4,705,690, issued Nov. 10, 1987.

The cloud/opacifier emulsion is prepared by mixing the clouding agent with the weighting agent (for opacifier emulsions), the emulsifier and water. The emulsion typically contains from about 0.1% to about 25% clouding agent, from about 1% to about 20% weighting oil agent (in the case of opacifier emulsions), from about 1% to about 30% emulsifiers, and from about 25% to about 97.9% water (or quantum satis).

The particle size of the water-insoluble components of the emulsion is reduced by employing a suitable apparatus known in the art. Because the ability of emulsifying agents to hold oil in suspension is proportional to particle size, emulsions of particles with diameters of about 0.1 to about 3.0 microns are suitable. Preferably, the particles are about 2.0 microns or less in diameter. Most preferred is an emulsion in which substantially all the particles are 1.0 microns or less in diameter. The particle size is reduced by passing the mixture through an homogenizer, colloid mill or turbine-type agitator. Usually one or two passes is sufficient. See e.g., Kupper et al., U.S. Pat. No. 4,705,691, issued Nov. 10,1987.

Flavor emulsions useful in beverage products of the present invention comprise one or more suitable flavor oils, extracts, oleoresins, essential oils and the like, known in the art for use as flavorants in beverages. This component can also comprise flavor concentrates such as those derived from concentration of natural products such as fruits. Terpeneless citrus oils and essences can also be used herein. Examples of suitable flavors include, for example, fruit flavors such as orange, lemon, lime and the like, cola flavors, tea flavors, coffee flavors, chocolate flavors, dairy flavors. These flavors can be derived from natural sources such as essential oils and extracts, or can be synthetically prepared. The flavor emulsion typically comprises a blend of various flavors and can be employed in the form of an emulsion, alcoholic extract, or spray dried. The flavor emulsion can also include clouding agents, with or without weighting agents, as previously described. See e.g., Kupper et al., U.S. Pat. No. 4,705,691, issued Nov. 10, 1987.

Flavor emulsions are typically prepared in the same manner as cloud/opacifier emulsions by mixing one or more flavoring oils (from about 0.001% to about 20%) with an emulsifying agent (from about 1% to about 30%) and water. (The oil clouding agents can also be present). Emulsions of particles with diameters of from about 0.1 to about 3.0 microns are suitable. Preferably, the particles are about 2.0 microns or less in diameter. Most preferably, the particles are about 1.0 microns or less in diameter. The emulsifying agent coats the particularized flavor oil to aid in preventing coalescence and in maintaining an appropriate dispersion. The viscosity and specific gravity of the flavor emulsion are regulated to be compatible with the finished beverage. See e.g., Kupper et al., U.S. Pat. No. 4,705,691, issued Nov. 10, 1987.

Flavor Agents

The compositions herein may optionally, but preferably, comprise one or more flavor agents. Preferably, such flavor agents are included in the beverage compositions and are typically selected from fruit juice, tea solids, milk solids, fruit flavors, botanical flavors, and mixtures thereof. Wherein fruit juice is included, the beverages of the present invention can comprise from about 0.1% to about 40%, preferably from about 1% to about 20%, more preferably from about 2% to about 10%, and most preferably from about 3% to about 6%, fruit juice. (As measured herein, the weight percentage of fruit juice is based on a single strength 2° to 16° Brix fruit juice). The fruit juice can be incorporated into the beverage as a puree, comminute, or as a single strength or concentrated juice. Especially preferred is incorporation of the fruit juice as a concentrate with a solids content (primarily as sugar solids) of from about 20° to about 80° Brix.

The fruit juice can be any citrus juice, non-citrus juice, or mixture thereof, which are known for use in dilute juice beverages. The juice can be derived from, for example, apple, cranberry, pear, peach, plum, apricot, nectarine, grape, cherry, currant, raspberry, gooseberry, elderberry, blackberry, blueberry, strawberry, lemon, lime, mandarin, orange, grapefruit, cupuacu, potato, tomato, lettuce, celery, spinach, cabbage, watercress, dandelion, rhubarb, carrot, beet, cucumber, pineapple, coconut, pomegranate, kiwi, mango, papaya, banana, watermelon, passion fruit, tangerine, and cantaloupe. Preferred juices are derived from apple, pear, lemon, lime, mandarin, grapefruit, cranberry, orange, strawberry, tangerine, grape, kiwi, pineapple, passion fruit, mango, guava, raspberry and cherry. Citrus juices, preferably grapefruit, orange, lemon, lime, and mandarin juices, as well as juices derived from mango, apple, passion fruit, and guava, as well as mixtures of these juices are most preferred.

Fruit flavors may also be utilized. As described above with respect to flavor emulsions, fruit flavors may be derived from natural sources such as essential oil and extracts, or can be synthetically prepared. Fruit flavors may be derived from fruits through processing, particularly concentrating. Wherein fruit juices are concentrated or evaporated, the water which is removed or the condensate contains volatile substances which comprise the flavor of the fruit. Often, such flavor is added to a juice concentrate to enhance the flavor thereof. The condensate may also be used to flavor "near waters" (lightly flavored water).

Botanical flavors may also be utilized. As used herein, the term "botanical flavor" refers to a flavor derived from parts of a plant other than the fruit; i.e., derived from nuts, bark, roots, and/or leaves. Also included within the term "botanical flavor" are synthetically prepared flavors made to simulate botanical flavors derived from natural sources. Botanical flavors can be derived from natural sources such as essential oils and extracts, or can be synthetically prepared. Suitable botanical flavors include jamaica, kola, marigold, chrysanthemum, chamomile, ginger, valerian, yohimbe, hops, eriodictyon, ginseng, bilberry, rice, red wine, mango, peony, lemon balm, nut gall, oak chip, lavender, walnut, gentiam, luo han guo, cinnamon, angelica, aloe, agrimony, yarrow and mixtures thereof.

Tannic acid or other similar acids can be used to provide an astringent taste to the beverage. From about 0.001% to about 10% tannic acid is used. Other flavor enhancers, as well as flavorants such as chocolate and vanilla can also be used.

Wherein tea solids are included, the beverages of the present invention can comprise from about 0.01% to about 1.2%, preferably from about 0.05% to about 0.8%, by weight of the beverage product, of tea solids. The term "tea solids" as used herein means solids extracted from tea materials including those materials obtained from the genus Camellia including *C. sinensis* and *C. assaimica*, for instance, freshly gathered tea leaves, fresh green tea leaves that are dried immediately after gathering, fresh green tea leaves that have been heat treated before drying to inactivate any enzymes present, unfermented tea, instant green tea, and partially fermented tea leaves. Green tea materials are tea leaves, tea plant stems, and other plant materials that are related and which have not undergone substantial fermentation to create black teas. Members of the genus Phyllanthus, *Catechu gambir* and Uncaria family of tea plants can also be used. Mixtures of unfermented and partially fermented teas can be used.

Tea solids for use in beverages of the present invention can be obtained by known and conventional tea solid extraction methods. A particularly preferred source of green tea solids can be obtained by the method described in Ekanayake et al., U.S. application Ser. No. 08/606,907, filed Feb. 26, 1996. Tea solids so obtained will typically comprise caffeine, theobromine, proteins, amino acids, minerals and carbohydrates. Suitable beverages containing tea solids can be formulated according to Tsai et al., U.S. Pat. No. 4,946, 701, issued Aug. 7, 1990. See also, Ekanayake et al., U.S. Pat. No. 5,427,806, issued Jun. 26,1995, for a suitable sources of green tea solids for use in the present invention.

Beverages according to the present invention may also comprise milk solids. These milk solids can be derived from various sources including whole milk, skim milk, condensed milk, and dried milk powder. As used herein, the term "milk" will be used to describe an aqueous dispersion of milk solids, such as fluid (whole or skim milk) or non-fat dry milk or condensed milk diluted with water. The amount of milk included typically ranges from about 5% to about 99.8%, preferably from about 5% to about 75%, more preferably from about 5% to about 40%, and most preferably from about 5% to about 15%. The amount of non-fat milk solids correlating to these levels of milk solids is in the range of from about 0.5% to about 8.2%, from about 0.5% to about 6.2%, from about 0.5% to about 3.3%, and from about 0.5% to 1.2% of the beverage, respectively.

Thickeners and Bulking Agents

Food and beverage compositions according to the present invention can further comprise one or more thickeners or bulking agents, including xanthan gum, carboxymethylcellulose, carboxyethylcellulose, hydroxypropylcellulose, methylcellulose, microcrystalline cellulose, starches, dextrins, fermented whey, tofu, maltodextrins, polyols, including sugar alcohols (e.g., sorbitol and mannitol), carbohydrates (e.g., lactose), propylene glycol alginate, gellan gum, guar gum, pectin, tragacanth gum, gum acacia, locust bean gum, gum arabic, gelatin, as well as mixtures of these thickeners. These thickeners and bulking agents are typically included in the compositions of the present invention at levels up to about 0.1%, depending on the particular thickener involved and the viscosity effects desired.

Sweeteners

The food and beverage compositions of the present invention can, and typically will, contain an effective amount of one or more sweeteners, including carbohydrate sweeteners and natural and/or artificial no/low calorie sweeteners. The amount of the sweetener used in the compositions of the present invention typically depends upon the particular sweetener used and the sweetness intensity desired. For no/low calorie sweeteners, this amount varies depending upon the sweetness intensity of the particular sweetener.

The compositions of the present invention can be sweetened with any of the carbohydrate sweeteners, preferably monosaccharides and/or disaccharides. Sweetened compositions, particularly beverages, will typically comprise from about 0.1% to about 20%, most preferably from about 6 to about 14%, sweetener. These sweeteners can be incorporated into the compositions in solid or liquid form but are typically, and preferably, incorporated as a syrup, most preferably as a concentrated syrup such as high fructose corn syrup. For purposes of preparing beverages of the present invention, these sugar sweeteners can be provided to some extent by other components of the beverage such as, for example, the fruit juice component and/or flavors.

Preferred sugar sweeteners for use in compositions of the present invention are sucrose, fructose, glucose, and mixtures thereof. Fructose can be obtained or provided as liquid fructose, high fructose corn syrup, dry fructose or fructose syrup, but is preferably provided as high fructose corn syrup. High fructose corn syrup (HFCS) is commercially available as HFCS-42, HFCS-55 and HFCS-90, which comprise 42%, 55% and 90%, respectively, by weight of the sugar solids therein, as fructose. Other naturally occurring sweeteners or their purified extracts, such as glycyrrhizin, the protein sweetener thaumatin, the juice of Luo Han Guo disclosed in, for example, Fischer et al., U.S. Pat. No. 5,433,965, issued Jul. 18, 1995, and the like can also be used in the compositions of the present invention.

Suitable no/low calorie sweeteners include saccharin, cyclamates, L-aspartyl-L-phenylalanine lower alkyl ester sweeteners (e.g., aspartame); L-aspartyl-D-alanine amides disclosed in Brennan et al., U.S. Pat. No. 4,411,925; L-aspartyl-D-serine amides disclosed in Brennan et al., U.S. Pat. No. 4,399,163; L-aspartyl-L-1-hydroxymethylalkaneamide sweeteners disclosed in Brand, U.S. Pat. No. 4,338,346; L-aspartyl-1-hydroxyethyalkaneamide sweeteners disclosed in Rizzi, U.S. Pat. No. 4,423,029; L-aspartyl-D-phenylglycine ester and amide sweeteners disclosed in Janusz, European Patent Application 168,112, published Jan. 15, 1986; N-[N-3,3-dimethylbutyl)-L-□-aspartyl]-L-phenylalanine 1-methyl ester sweeteners disclosed in Gerlat et al., WO 99/30576, assigned to The Nutrasweet Co., published Jun. 24, 1999; alltame, thaumatin; dihydrochalcones; cyclamates; steviosides; glycyrrhizins, synthetic alkoxy aromatics, such as Dulcin and P-4000; sucrolose; suosan; miraculin; monellin; sorbitol, xylitol; talin; cyclohexylsulfamates; substituted imidazolines; synthetic sulfamic acids such as acesulfame, acesulfame-K and n-substituted sulfamic acids; oximes such as perilartine; rebaudioside-A; peptides such as aspartyl malonates and succanilic acids; dipeptides; amino acid based sweeteners such as gem-diaminoalkanes, meta-aminobenzoic acid, L-aminodicarboxylic acid alkanes, and amides of certain alpha-aminodicarboxylic acids and gem-diamines; and 3-hydroxy-4-alkyloxyphenyl aliphatic carboxylates or heterocyclic aromatic carboxylates; and the like and mixtures thereof. A particularly preferred low calorie sweetener is aspartame.

Coloring Agent

Small amounts of coloring agents may be utilized in the compositions of the present invention. FD&C dyes (e.g., yellow #5, blue #2, red #40) and/or FD&C lakes are preferably used. By adding the lakes to the other powdered ingredients, all the particles, in particular the colored iron compound, are completely and uniformly colored and a uniformly colored composition is attained. Preferred lake dyes which may be used in the present invention are the FDA-approved Lake, such as Lake red #40, yellow #6, blue #1, and the like. Additionally, a mixture of FD&C dyes or a FD&C lake dye in combination with other conventional food and food colorants may be used. Riboflavin and □-carotene may also be used. The exact amount of coloring agent used will vary, depending on the agents used and the intensity desired in the finished product. The amount can be readily determined by one skilled in the art. Generally, if utilized, the coloring agent should be present at a level of from about 0.0001% to about 0.5%, preferably from about 0.001% to about 0.1%, and most preferably from about 0.004% to about 0.1%, by weight of the composition.

Nutrients

The compositions herein (particularly the food and beverage compositions) can be fortified with one or more nutrients, especially one or more vitamins, minerals, and/or amino acids. The U.S. Recommended Daily Intake (USRDI) for vitamins and minerals are defined and set forth in the Recommended Daily Dietary Allowance-Food and Nutrition Board, National Academy of Sciences-National Research Council.

Any amino acid may be utilized herein, especially the naturally occurring amino acids. Preferred amino acids for inclusion herein are L-lysine and L-carnitine, particularly L-lysine.

Unless otherwise specified herein, wherein a given mineral is present in the product, the product comprises at least about 1%, preferably at least about 5%, more preferably from about 10% to about 200%, even more preferably from about 40% to about 150%, and most preferably from about 60% to about 125% of the USRDI of such mineral. Unless otherwise specified herein, wherein a given vitamin is present in the product, the product comprises at least about 1%, preferably at least about 5%, more preferably from about 10% to about 200%, even more preferably from about 20% to about 150%, and most preferably from about 25% to about 120% of the USRDI of such vitamin.

Non-limiting examples of such vitamins and minerals include iron, zinc, copper, calcium, phosphorous, niacin, thiamin, folic acid, pantothenic acid, iodine, vitamin A, vitamin C, vitamin $B_2$, vitamin $B_3$, vitamin $B_6$, vitamin $B_{12}$, vitamin D, vitamin E, and vitamin K. Preferably, wherein a vitamin or mineral is utilized the vitamin or mineral is selected from iron, zinc, calcium, niacin, thiamin, folic acid, iodine, vitamin A, vitamin C, vitamin $B_6$, vitamin $B_{12}$, vitamin D, and vitamin E. A particularly preferred mineral for use herein is calcium.

Commercially available vitamin A sources may also be included in the present compositions. Vitamin A can be provided, for example, as vitamin A palmitate (retinol palmitate) and/or as beta-carotene. The vitamin A may be in the form of, for example, an oil, beadlets or encapsulated. As used herein, "vitamin A" includes, but is not limited to, vitamin A, β-carotene, retinol palmitate, and retinol acetate. Wherein vitamin A is present in the compositions herein, the product comprises at least about 1%, preferably at least about 5%, more preferably from about 10% to about 200%, even more preferably from about 15% to about 150%, and most preferably from about 20% to about 120% of the USRDI of such vitamin. Wherein vitamin A is present in the products herein, it is especially preferred to include about 25% of the USRDI of vitamin A. The quantity of vitamin A to be added is dependent on processing conditions and the amount of vitamin A deliver desired after storage. Preferably, wherein vitamin A is included within the present compositions, the products comprise from about 0.0001% to about 0.2%, more preferably from about 0.0002% to about 0.12%, also preferably from about 0.0003% to about 0.1%, even more preferably from about 0.0005% to about 0.08%, and most preferably from about 0.001% to about 0.06% of vitamin A, by weight of the composition.

Commercially available sources of vitamin $B_2$ (also known as riboflavin) may be utilized in the present compositions. Wherein vitamin $B_2$ is present in the compositions herein, the product comprises at least about 1%, preferably at least about 5%, more preferably from about 5% to about 200%, even more preferably from about 10% to about 150%, and most preferably from about 10% to about 120% of the USRDI of such vitamin. Wherein vitamin $B_2$ is present in the compositions herein, it is especially preferred to include from about 15% to about 35% of the USRDI of vitamin $B_2$.

Commercially available sources of vitamin C can be used herein. Encapsulated ascorbic acid and edible salts of ascorbic acid can also be used. Wherein vitamin C is present in the products herein, the product comprises at least about 1%, preferably at least about 5%, more preferably from about 10% to about 200%, even more preferably from about 20% to about 150%, and most preferably from about 25% to about 120% of the USRDI of such vitamin. Wherein vitamin C is present in the compositions herein, it is especially preferred to include about 100% of the USRDI of vitamin C. The quantity of vitamin C to be added is dependent on processing conditions and the amount of vitamin C deliver desired after storage. Preferably, wherein vitamin C is included within the present compositions, the compositions comprise from about 0.005% to about 0.2%, more preferably from about 0.01% to about 0.12%, also preferably from about 0.02% to about 0.1%, even more preferably from about 0.02% to about 0.08%, and most preferably from about 0.03% to about 0.06% of vitamin C, by weight of the composition.

Commercial sources of iodine, preferably as an encapsulated iodine may be utilized herein. Other sources of iodine include iodine-containing salts, e.g., sodium iodide, potassium iodide, potassium iodate, sodium iodate, or mixtures thereof. These salts may be encapsulated.

Nutritionally supplemental amounts of other vitamins which may be incorporated herein include, but are not limited to, vitamins $B_6$ and $B_{12}$, folic acid, niacin, pantothenic acid, folic acid, vitamin D, and vitamin E. Wherein the composition comprises one of these vitamins, the product preferably comprises at least 5%, preferably at least 25%, and most preferably at least 35% of the USRDI for such vitamin.

Minerals which may optionally be included in the composition herein are, for example, magnesium, zinc, iodine, iron, and copper. Any soluble salt of these minerals suitable for inclusion edible products can be used, for example, magnesium citrate, magnesium gluconate, magnesium sulfate, zinc chloride, zinc sulfate, potassium iodide, copper sulfate, copper gluconate, and copper citrate.

Calcium is a particularly preferred mineral for use in the present invention. Preferred sources of calcium include, for example, amino acid chelated calcium, calcium carbonate, calcium oxide, calcium hydroxide, calcium sulfate, calcium chloride, calcium phosphate, calcium hydrogen phosphate, calcium dihydrogen phosphate, calcium citrate, calcium malate, calcium titrate, calcium gluconate, calcium realate, calcium tantrate, and calcium lactate, and in particular calcium citrate-malate. The form of calcium citrate-malate is described in, e.g., Mehansho et al., U.S. Pat. No. 5,670,344, issued Sep. 23, 1997; Diehl et al., U.S. Pat. No. 5,612,026, issued Mar. 18, 1997; Andon et al., U.S. Pat. No. 5,571,441, issued Nov. 5, 1996; Meyer et al., U.S. Pat. No. 5,474,793, issued Dec. 12, 1995; Andon et al., U.S. Pat. No. 5,468,506, issued Nov. 21, 1995; Burkes et al., U.S. Pat. No. 5,445,837, issued Aug. 29, 1995; Dake et al., U.S. Pat. No. 5,424,082, issued Jun. 13, 1995; Burkes et al., U.S. Pat. No. 5,422,128, issued Jun. 6, 1995; Burkes et al., U.S. Pat. No. 5,401,524, issued Mar. 28, 1995; Zuniga et al., U.S. Pat. No. 5,389,387, issued Feb. 14, 1995; Jacobs, U.S. Pat. No. 5,314,919, issued May 24, 1994; Saltman et al., U.S. Pat. No. 5,232,709, issued Aug. 3, 1993; Camden et al., U.S. Pat. No. 5,225,221, issued Jul. 6, 1993; Fox et al., U.S. Pat. No. 5,215,769, issued Jun. 1, 1993; Fox et al., U.S. Pat. No. 5,186,965, issued Feb. 16, 1993; Saltman et al., U.S. Pat. No. 5,151,274, issued Sep. 29, 1992; Kochanowski, U.S. Pat. No. 5,128,374, issued Jul. 7, 1992; Mehansho et al., U.S. Pat. No. 5,118,513, issued Jun. 2, 1992; Andon et al., U.S. Pat. No. 5,108,761, issued Apr. 28, 1992; Mehansho et al., U.S. Pat. No. 4,994,283, issued Feb. 19, 1991; Nakel et al., U.S. Pat. No. 4,786,510, issued Nov. 22, 1988; and Nakel et al., U.S. Pat. No. 4,737,375, issued Apr. 12, 1988. Preferred compositions of the present invention will comprise from about 0.01% to about 0.5%, more preferably from about 0.03% to about 0.2%, even more preferably from about 0.05% to about 0.15%, and most preferably from about 0.1% to about 0.15% of calcium, by weight of the composition.

Iron may also be utilized in the compositions of the present invention. Acceptable forms of iron are well-known in the art. The amount of iron compound incorporated into the composition will vary widely depending upon the level of supplementation desired in the final product and the targeted consumer. Iron fortified compositions of the present invention typically contain from about 5% to about 100%, preferably from about 15% to about 50%, and most preferably about 20% to about 40% of the USRDI for iron.

Ferrous iron is typically better utilized by the body than ferric iron. Highly bioavailable ferrous salts that can be used in the ingestible compositions of the present invention are ferrous sulfate, ferrous fumarate, ferrous succinate, ferrous gluconate, ferrous lactate, ferrous tartarate, ferrous citrate, ferrous amino acid chelates, as well as mixtures of these ferrous salts. While ferrous iron is typically more bioavailable, certain ferric salts can also provide highly bioavailable sources of iron. Highly bioavailable ferric salts that can be used in the food or beverage compositions of the present invention are ferric saccharate, ferric ammonium citrate, ferric citrate, ferric sulfate, as well as mixtures of these ferric salts. Combinations or mixtures of highly bioavailable ferrous and ferric salts can be used in these edible mixes and ready-to-serve beverages. The preferred sources of highly bioavailable iron are ferrous fumarate and ferrous amino acid chelates.

Ferrous amino acid chelates particularly suitable as highly bioavailable iron sources for use in the present invention are those having a ligand to metal ratio of at least 2:1. For example, suitable ferrous amino acid chelates having a ligand to metal mole ratio of two are those of formula:

$$Fe(L)_2$$

where L is an alpha amino acid, dipeptide, tripeptide, or quadrapeptide ligand. Thus, L can be any ligand which is a naturally occurring alpha amino acid selected from alanine, arginine, asparagine, aspartic acid, cysteine, cystine, glutamine, glutamic acid, glycine, histidine, hydroxyproline, isoleucine, leucine, lysine, methionine, ornithine, phenylalanine, proline, serine, threonine, tryptophan, tyrosine, and valine; or dipeptides, tripeptides, or quadrapeptides formed by any combination of these alpha amino acids. See e.g., Ashmead et al., U.S. Pat. No. 4,863,898, issued Sep. 5, 1989; Ashmead, U.S. Pat. No. 4,830,716, issued May 16, 1989; and Ashmead, U.S. Pat. No. 4,599,152, issued Jul. 8, 1986, all of which are incorporated by reference. Particularly preferred ferrous amino acid chelates are those where the reacting ligands are glycine, lysine, and leucine. Most preferred is the ferrous amino acid chelate sold under the mark Ferrochel® (Albion Laboratories, Salt Lake City, Utah) wherein the ligand is glycine.

In addition to these highly bioavailable ferrous and ferric salts, other sources of bioavailable iron can be included in the food and beverage compositions of the present invention. Other sources of iron particularly suitable for fortifying products of the present invention included certain iron-sugar-carboxylate complexes. In these iron-sugar-carboxylate complexes, the carboxylate provides the counterion for the ferrous (preferred) or ferric iron. The overall synthesis of these iron-sugar-carboxylate complexes involves the formation of a calcium-sugar moiety in aqueous media (for example, by reacting calcium hydroxide with a sugar, reacting the iron source (such as ferrous ammonium sulfate) with the calcium-sugar moiety in aqueous media to provide an iron-sugar moiety, and neutralizing the reaction system with a carboxylic acid (the "carboxylate counterion") to provide the desired iron-sugar-carboxylate complex. Sugars that can be used to prepare the calcium-sugar moiety include any of the ingestible saccharidic materials, and mixtures thereof, such as glucose, sucrose and fructose, mannose, galactose, lactose, maltose, and the like, with sucrose and fructose being the more preferred. The carboxylic acid providing the "carboxylate counterion" can be any ingestible carboxylic acid such as citric acid, malic acid tartaric acid, lactic acid, succinic acid, propionic acid, etc., as well as mixtures of these acids.

These iron-sugar-carboxylate complexes can be prepared in the manner described in, e.g., Nakel et al., U.S. Pat. Nos. 4,786,510 and 4,786,518, issued Nov. 22, 1988, both of which are incorporated by reference. These materials are referred to as "complexes", but they may exist in solution as complicated, highly hydrated, protected colloids; the term "complex" is used for the purpose of simplicity.

Zinc may also be utilized in the compositions of the present invention. Acceptable forms of zinc are well-known in the art. Zinc fortified products of the present invention typically contain from about 5% to about 100%, preferably from about 15% to about 50%, and most preferably about 25% to about 45% of the USRDI for zinc. The zinc compounds which can be used in the present invention can be in any of the commonly used forms such as, e.g., zinc sulfate, zinc chloride, zinc acetate, zinc gluconate, zinc ascorbate, zinc citrate, zinc aspartate, zinc picolinate, amino acid chelated zinc, and zinc oxide. Zinc gluconate and amino acid chelated zinc are particularly preferred.

Carbonation Component

Carbon dioxide can be introduced into the water which is mixed with a beverage syrup or into the dilute beverage after dilution to achieve carbonation. The carbonated beverage can be placed into a container, such as a bottle or can, and then sealed. Any conventional carbonation methodology may be utilized to make carbonated beverage products of this invention. The amount of carbon dioxide introduced into the beverage will depend upon the particular flavor system utilized and the amount of carbonation desired.

pH

The compositions of the present invention, particularly the beverage compositions, preferably have a pH of from about 2 to about 8, more preferably from about 2 to about 4.5, and most preferably from about 2.7 to about 4.2. Beverage acidity can be adjusted to and maintained within the requisite range by known and conventional methods, e.g., the use of food grade acid buffers. Typically, beverage acidity within the above recited ranges is a balance between maximum acidity for microbial inhibition and optimum acidity for the desired beverage flavor. Food compositions preferably have a pH of less than about 8.

Non-Caloric or Reduced Calorie Fats

The compositions can be used in combination with non-caloric or reduced calorie fats, such as branched chain fatty acid triglycerides, triglycerol ethers, polycarboxylic acid esters, sucrose polyesters, sucrose polyethers, neopentyl alcohol esters, silicone oils/siloxanes, and dicarboxylic acid esters (particularly where the composition is a food composition). Other partial fat replacements useful in combination with the fat materials are medium chain triglycerides, highly esterified polyglycerol esters, acetin fats, polyoxyethylene esters, jojoba esters, mono/diglycerides of fatty acids, and mono/diglycerides of short-chain dibasic acids.

Fiber Component

Similarly, food and beverage compositions can be made that combine the present compositions with dietary fibers to achieve the combined benefits of each. By "dietary fiber" is meant complex carbohydrates resistant to digestion by mammalian enzymes, such as the carbohydrates found in plant cell walls and seaweed, and those produced by microbial fermentation. Examples of these complex carbohydrates are brans, celluloses, hemicelluloses, pectins, gums and mucilages, seaweed extract, and biosynthetic gums. Sources of the cellulosic fiber include vegetables, fruits, seeds, cereals, and man-made fibers (for example, by bacterial synthesis). Commercial fibers such as purified plant cellulose, or cellulose flour, can also be used. Naturally occurring fibers include fiber from whole citrus peel, citrus albedo, sugar beets, citrus pulp and vesicle solids, apples, apricots, and watermelon rinds.

These dietary fibers may be in a crude or purified form. The dietary fiber used may be of a single type (e.g., cellulose), a composite dietary fiber (e.g., citrus albedo fiber containing cellulose and pectin), or some combination of fibers (e.g., cellulose and a gum). The fibers can be processed by methods known to the art.

Primarily due to the present compositions, the foods and beverages herein can provide reduced serum cholesterol and thus reduced risk of heart disease. Additionally, the present compositions have acceptable organoleptic properties, particularly flavor and texture, despite the presence of L-arginine, polypeptides thereof, salts thereof, and proforms thereof.

Dietary foods can be made with the compositions to meet special dietary needs, for example, of persons who are obese, diabetic, or hypercholesterolemic. The present compositions can be a major part of a low-fat, low-calorie, low-cholesterol diet, or may supplement a normal diet, and they can be used alone or in combination with drug therapy, nutritional therapy, or other therapy. Combinations of food or beverage products made with the compositions can be used as part of a total dietary management regimen, based on one or more of these products, containing the compositions alone or in combination with one or more of the above-mentioned ingredients, to provide one or more of the above-mentioned benefits.

This discussion of the composition uses, combinations, and benefits, is not intended to be limiting or all-inclusive. It is contemplated that other similar uses and benefits can be found that will fall within the spirit and scope of this invention.

EXAMPLES

The following examples are illustrative of uses of the present compositions. Such examples are non-limiting illustrations and various modifications thereof may be made by one of ordinary skill in the art with the benefit of the present disclosure.

Example 1

A fat free health bar is prepared having the following composition:

| Component | Wt % |
| --- | --- |
| Soy Protein Isolates | 28 |
| Fructose | 25 |
| High Fructose Corn Syrup | 23.5 |
| Raisins | 6.8 |
| Sterol Ester of L-arginine | 10 |
| Olean ™ (sucrose polyester, commercially available from Procter & Gamble Co., Cincinnati, OH) | 6 |
| Cinnamon | 0.5 |
| Salt | 0.1 |
| Sodium Bicarbonate | 0.1 |

The Sterol ester of L-arginine and Olean™ are pre-mixed prior to blending with the remainder of the dry ingredients and formed into bars. Other dried fruits, for example, cranberries, apricots, and the like may be substituted for the raisins. The health bar is ingested once daily for a period of 12 weeks as a supplement to a normal diet. The health bar is shown to reduce serum cholesterol levels after this 12 week period.

Example 2
A sports energy gel is prepared having the following composition:

| Component | Wt % |
| --- | --- |
| Maltodextrin | 54 |
| Water | 20 |
| Fructose | 12 |
| Sterol Ester of L-arginine | 10 |
| Citric Acid | 3 |
| Vitamin C | 0.5 |
| Vitamin A | 0.1 |

| Component | Wt % |
| --- | --- |
| Artificial Flavor | 0.2 |
| Sodium Benzoate | 0.1 |
| Potassium Sorbate | 0.1 |

All components are combined and heated for pasteurization.

Example 3

A health shake suitable for use as a dietary supplement or meal replacement is prepared having the following composition:

| Component | Wt % |
| --- | --- |
| Fat Free Milk | 52.5 |
| Vitamin E Ester of L-arginine | 10 |
| Water | 18.5 |
| Sugar | 5 |
| Fructose | 5 |
| Cocoa | 3 |
| Gum Arabic | 2 |
| Cellulose Gel | 2 |
| Canola Oil | 1 |
| Potassium Phosphate | 0.3 |
| Dextrose | 0.3 |
| Lecithin | 0.1 |
| Mono- and Diglycerides | 0.1 |
| Carrageenan | 0.1 |
| Vitamin and Mineral Mix | 0.1 |

*vitamin A, C, D, E, B-vitamins (B1, B2, B6, B12, Folate, and niacin), with minerals of iron and zinc The finished composition can be canned or subjected to Ultra High Temperature (UHT) pasteurization by heating to 135–150° C. for 5 seconds and then aseptically packaged to provide a ready-to-serve beverage.

Example 4

A powder chocolate drink having the following composition is made by the process as described in Mehansho et al. U.S. Pat. Nos. 5,888,563 and 5,707,670. The di-substituted glycerol ester of L-arginine is co-mixed with the lecithin as described to reduce the negative flavor associated with L-arginine.

| Component | Wt % |
| --- | --- |
| Sugar | 55.5 |
| Disubstituted glycerol ester of L-arginine | 11.2 |
| Non-fat dry milk | 15 |
| Sodium Chloride | 0.43 |
| Cocoa Powder (14% fat) | 16.4 |
| Colors | 0.07 |
| Butylated Hydroxytoluene (BHT) | 0.1 |
| Vitamin/Mineral Mix* | 0.55 |
| Ferrous Fumarate | 0.06 |
| Artificial Chocolate Flavor | 0.3 |
| Lecithin | 0.35 |
| Stabilizer (cholesterol) | 0.04 |

*vitamin A, C, D, E, B-vitamins (B1, B2, B6, B12, Folate, and niacin), with minerals of iron and zinc

What is claimed is:

1. A composition comprising:
   (a) a compound having the structure:

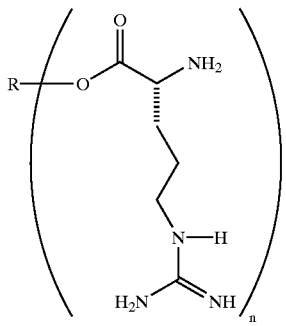

or salts, polypeptides, and pro-forms thereof, wherein R is selected from the group consisting of:
   (1) sterols; wherein n is 1;
   (2) stanols; wherein n is 1; and
   (b) at least one nutrient selected from the group consisting of vitamins and minerals, wherein the composition is a beverage composition which exhibits a pH of less than about 5 when the beverage composition is constituted with aqueous fluid.

2. A composition according to claim 1 further comprising water.

3. A composition according to claim 2 further comprising at least one component selected from the group consisting or fruit juice, tea solids, milk solids, fruit flavors, botanical flavors, and mixtures thereof.

4. A composition according to claim 3 wherein at least one of the nutrients is selected from the group consisting of iron, zinc, copper, calcium, phosphorous, niacin, thiamin, folic acid, pantothenic acid, iodine, vitamin A, vitamin C, vitamin $B_2$, vitamin $B_3$, vitamin $B_6$, vitamin $B_{12}$, vitamin D, vitamin E and vitamin K.

5. A composition according to claim 4 at least one of the nutrients is vitamin C.

6. A kit comprising a composition according to claim 1 and information that the kit provides one or benefits selected from the group consisting of cardiovascular benefits and organoleptic benefits.

7. A kit according to claim 6 where at least one benefit is a cardiovascular benefit.

* * * * *